United States Patent [19]

Hoefle

[11] Patent Number: 4,737,512

[45] Date of Patent: Apr. 12, 1988

[54] 4-(SUBSTITUTED-ISOINDOL-2-YL)PHENOXY-PENTANOIC AND -HEPTANOIC ACIDS AND DERIVATIVES AS ANTI-ARTERIOSCLEROTIC AGENTS

[75] Inventor: Milton L. Hoefle, Ann Arbor, Mich.

[73] Assignee: Warner-Lambert Company, Morris Plains, N.J.

[21] Appl. No.: 923,520

[22] Filed: Oct. 27, 1986

[51] Int. Cl.$^4$ ..................... A61K 31/40; C07D 209/48
[52] U.S. Cl. .................................... 514/417; 514/421; 548/476; 548/513
[58] Field of Search ................ 548/476, 513; 514/417, 514/421

[56] References Cited

U.S. PATENT DOCUMENTS

| 3,804,839 | 4/1974 | Dahm et al. | 548/482 |
| 3,978,080 | 8/1976 | Carney | 548/512 |

FOREIGN PATENT DOCUMENTS

| 68822 | 1/1983 | European Pat. Off. | 548/476 |
| 130077 | 2/1985 | European Pat. Off. | |
| 172147 | 2/1986 | European Pat. Off. | |
| 215424 | 3/1987 | European Pat. Off. | 548/476 |

OTHER PUBLICATIONS

Derwent Abstract of Great Britain Patent No. 2,082,569 published Mar. 10, 1982.
Derwent Abstract of Japanese Patent No. 45 6115773, published Sep. 11, 1981.
M. Artico et al., Biochem. Pharmacology, vol. 17, pp. 893–898 (1968).
American Journal of Medicine, vol. 62, pp. 707–714, Gordon, T. et al., High Density Lipoprotein as a Protective Factor Against Coronary Heart Disease, May '77.
Jama 251:361 and 365 (1984).
Journal of Medicinal Chemistry, 1985, vol. 28, No. 1 pp. 10–12 Comparison of the Hypolipidemic Activity of Cyclic vs. Acyclic Imides, P. Josee Voorstad, et al.

*Primary Examiner*—Mary E. Ceperley
*Attorney, Agent, or Firm*—Elizabeth M. Anderson

[57] ABSTRACT

Novel 4-(substituted-isoindol-2-yl)phenoxy-pentanoic and -heptanoic acids and derivatives which are useful as anti-arteriosclerotic agents are disclosed. The compounds elevate the high density lipoprotein fraction of cholesterol and also lower the low density lipoprotein fraction of cholesterol. Methods for preparing and using the compounds are included.

15 Claims, No Drawings

4-(SUBSTITUTED-ISOINDOL-2-YL)PHENOXY-PENTANOIC AND -HEPTANOIC ACIDS AND DERIVATIVES AS ANTI-ARTERIOSCLEROTIC AGENTS

BACKGROUND OF THE INVENTION

Elevated levels of blood cholesterol and blood lipids are conditions which are believed related to the onset of arteriosclerosis. Thus, compounds capable of reducing the levels of these blood constituents are recognized as potentially useful antiarteriosclerotic agents.

The compounds of the present invention are useful as anti-arteriosclerotic agents and are capable of elevating the high density lipoprotein fraction of cholesterol (HDL-C), and this effect is known to lower the risk factor of coronary heart disease (Gordon, T. et al, High Density Lipoprotein as a Protective Factor Against Coronary Heart Disease, May 1977, The American Journal of Medicine, Vol. 62, pp. 707–714). There is strong support for the concept that induced lowering of LDL will reduce the risk for coronary heart disease in hypocholesteremic patients (JAMA 251: 361 and 365, 1984). Certain compounds of the invention also are able to reduce the low density lipoprotein fraction of cholesterol (LDL-cholesterol), thus further reducing the risk factor of coronary heart disease.

British Application No. 2,082,569 discloses certain phthalimides used as antiarrhythmic agents and local anesthetics.

Japanese Application No. 56/15773 covers phthalimide derivatives which exhibit anticomplement activity.

SUMMARY

One aspect of the present invention is a compound of the formula

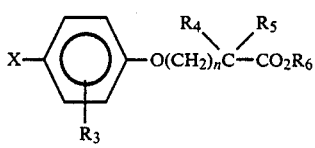

wherein X is

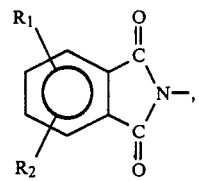

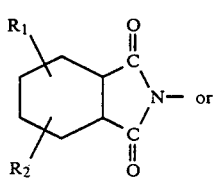

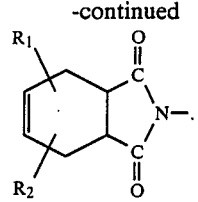

wherein $R_1$ and $R_2$ are the same or different and are hydrogen, halogen, a straight or branched alkyl group of from one to six carbon atoms, an alkoxy group of from one to six carbon atoms, or $CF_3$; $R_3$ is hydrogen or an alkyl group of from one to four carbon atoms; n is an integer of from three to five; $R_4$ and $R_5$ are the same or different and are a straight or branched alkyl of from one to six carbon atoms or when taken together are —$(CH_2)_m$— wherein m is an integer of from two to five; $R_6$ is hydrogen or an alkyl of from one to six carbon atoms, or a pharmaceutically acceptable base salt thereof.

Another aspect of the present invention is a method of preparing a compound of formula I above which comprises reacting a substituted 1,3-dioxo-2H-isoindol-2-yl-phenol with a halogenated, alkyl-substituted carboxylic acid ester.

A third aspect of the present invention is a pharmaceutical composition, useful for treating arteriosclerosis in a mammal, which comprises an effective amount of a compound of formula I above in combination with a pharmaceutically acceptable carrier.

A fourth aspect of the present invention is a method of treating arteriosclerosis in mammals which comprises administering an effective amount of the above defined pharmaceutical composition to said mammal.

DETAILED DESCRIPTION

Compounds of formula I

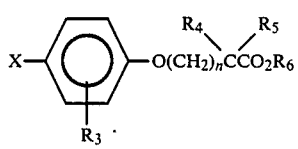

wherein X is

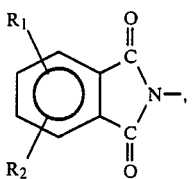

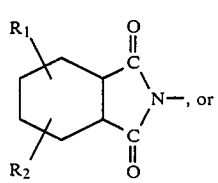

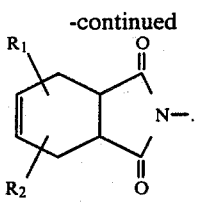

described above, comprise the present invention.

The compounds of the invention wherein $R_6$ is hydrogen form pharmaceutically acceptable salts with both organic and inorganic bases.

Examples of suitable bases for salt formation are sodium hydroxide, sodium carbonate, sodium bicarbonate, potassium hydroxide, calcium hydroxide, ammonia, organic amines and the like. The salts are prepared by contacting the free acid form with an equivalent amount of the desired base in the conventional manner. The free acid forms may be regenerated by treating the salt form with an acid. For example, dilute aqueous acid solutions may be utilized. Dilute aqueous hydrochloric acid, sulfuric acid or acetic acid are suitable for this purpose. The free acid forms differ from their respective salt forms somewhat in certain physical properties such as solubility in polar solvents, but the salts are otherwise equivalent to their respective free acid forms for purposes of the invention.

The compounds of the invention can exist in unsolvated as well as solvated forms, including hydrated forms. In general, the solvated forms, with pharmaceutically acceptable solvents such as water, ethanol and the like are equivalent to the unsolvated forms for purposes of the invention.

The term halogen is intended to include fluorine, chlorine, bromine and iodine. The alkyl and alkoxy groups contemplated by the invention comprise both straight and branched carbon chains of from one to about six carbon atoms. Representative of such groups are methyl, ethyl, isopropyl, butyl, pentyl, 3-methylpentyl, methoxy, ethoxy, i-propoxy, t-butoxy, n-hexoxy, 3-methylpentoxy and the like.

The preferred compounds are those of formula I where X=structures A, B, or C and $R_1$ and $R_2$ are the same or different and are hydrogen or halogen, $R_3$ is hydrogen; $R_4$ and $R_5$ are the same or different and are an alkyl of from one to four carbon atoms, $R_6$ is hydrogen or an alkyl of from one to six carbon atoms, and n is an integer from three to five.

The more preferred compounds are those of formula I where X=structures A or B and $R_1$ and $R_2$ are hydrogen, $R_3$ is hydrogen; n is three or five, $R_4$ and $R_5$ are methyl, and $R_6$ is hydrogen or an alkyl of from one to two carbon atoms.

The most preferred compounds are:
methyl 5-[4-(1,3-dihydro-1,3-dioxo-2H-isoindol-2-yl)phenoxy]-2,2-dimethylpentanoate;
methyl 7-[4-(1,3-dihydro-1,3-dioxo-2H-isoindol-2-yl)phenoxy]-2,2-dimethylheptanoate; and
methyl-2,2-dimethyl-5-[4-octahydro-1,3-dioxo-2H-isoindol-2-yl]phenoxypentanoate.

The above compounds may be prepared by reacting a substituted 1,3-dioxo-2H-isoindol-2-yl-phenol with a halogenated, alkyl-substituted carboxylic acid ester in solvent at room temperature.

In the preferred reaction the substituted phenol is dissolved in dimethylformamide at room temperature. Sodium hydride is added in portions, and then the halogenated carboxylic acid ester is added. The reaction proceeds at room temperature for from 12 to 24 hours. The reaction mixture is then heated for from two to six hours after which the solvent is removed and the product is collected. Alternatively sodium methoxide is used in place of sodium hydride.

The compounds of the invention are new chemical substances of value as pharmacological agents for the treatment of arteriosclerosis in warm-blooded animals. The anti-arterioslcerotic activity of representative compounds of the invention was established by the screening procedure described in Maxwell, R. E., Nawrocki, J. W., and Uhlendorf, P. D., Artery, 1, 303 (1978). This procedure is incorporated by reference herein. Utilizing this procedure, the following results were obtained for representative compounds of this invention. See Table I below.

TABLE I

| Compound Number | n | Elevation* HDL / HDL gemfibrozil | Reduction* LDL / LDL gemfibrozil |
|---|---|---|---|
| 1 | 3 | 0.4 | 0.5 |
| 2 | 5 | 1.2 | 0.9 |
| 3 | 3,4,5,6,7,8,9 hexahydro | 1.3 | 0.7 |

*The elevation of HDL and the reduction of LDL is expressed as a ratio of effect of the test compound with the effect of gemfibrozil which was used as a control in this test. Gemfibrozil has been shown to elevate HDL and to lower LDL in man. [Manninen, Vesa, The Gemfibrozil Study, 1985, Acta Med. Scand. (Supplement), Vol. 701, pp 83–89].

The compounds of the invention can be prepared and administered in a wide variety of oral and parenteral dosage forms. It will be clear to those skilled in the art that the following dosage forms may comprise as the active component, either a compound of formula I, or a corresponding pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methyl cellulose, sodium carboxymethyl cellulose and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampules. The unit dosage form can also be a capsule, cachet or tablet itself or it can be the appropriate number of any of these packaged form.

The quantity of active compound in a unit dose of preparation may be varied or adjusted from 1 mg to 300 mg according to the particular application and the potency of the active ingredient.

In therapeutic use as agents for treating arteriosclerosis, the compounds utilized in the pharmaceutical method of this invention are administered at the initial dosage of about 10 mg to about 100 mg per kilogram daily. A daily dose range of about 10 mg to about 30 mg per kilogram is preferred. The dosages, however, may be varied depending upon the requirements of the patient, the severity of the condition being treated and the compound being employed. Determination of the proper dosage for a particular situation is within the skill of the art. For convenience, the total daily dosage may be divided and administered in portions during the day if desired.

The compounds of the present invention are useful as anti-arteriosclerotic agents. These compounds elevate the high density lipoprotein fraction of cholesterol and also lower the low density lipoprotein fraction of cholesterol.

The following examples are provided to enable one skilled in the art to practice the present invention. These examples are not intended to limit in any way the scope of the invention, but are illustrative thereof.

EXAMPLE 1

Methyl 5-[4-(1,3-dihydro-1,3-dioxo-2H-isoindol-2-yl)phenoxy]-2,2-dimethylpentanoate A solution of 30 g of phthalic anhydride, 22 g of p-aminophenol, and 100 ml DMF was heated on a steam bath for three hours and then poured into 500 ml of $H_2O$. The solid product, N-[p-hydroxyphenyl]phthalimide, was collected by filtration and then suspended and stirred in cold EtOH (75 ml) and collected by filtration; 42.7 g; mp 292°–4° C. (literature mp 288° C.).

The above product (8.43 g) was dissolved in 100 ml of DMF and 1.2 g of NaH (50% dispersion) was added in portions. Following the addition the solution was stirred for one hour at room temperature and then 5.6 g of methyl 5-bromo-2,2-dimethylpentanoate was added. The reaction mixture was stirred at room temperature overnight. The next morning it was heated on a steam bath for one hour, cooled, and concentrated on rotary evaporator under reduced pressure. $H_2O$ was added to residue which solidified on standing. The product was purified by two recrystallization from EtOAc; mp 118°–9° C.

Calcd. for $C_{22}H_{23}NO_5$ (381.41), C, 69.27; H, 6.08; N, 3.67; Found C, 69.27; H, 6.37; N, 3.55.

Compounds made by the same method as in Example 1 are:
methyl 5-[4-(5-chloro-1,3-dihydro-1,3-dioxo-2H-isoindol-2-yl)phenoxy]-2,2-dimethylpentanoate;
methyl 5-[4-(5,6-dichloro-1,3-dihydro-1,3-dioxo-2H-isoindol-2-yl)phenoxy]-2,2-dimethylpentanoate;
methyl 5-[4-(1,3-dihydro-4-methyl-1,3-dioxo-2H-isoindol-2-yl)phenoxy]-2,2-dimethylpentanoate;
methyl 5-[4-(1,3-dihydro-4,5-dimethyl-1,3-dioxo-2H-isoindol-2-yl)phenoxy]-2,2-dimethylpentanoate;
methyl 5-[4-(1,3-dihydro-4,5-dimethoxy-1,3-dioxo-2H-isoindol-2-yl)phenoxy]-2,2-dimethylpentanoate;
methyl 5-[4-(1,3-dihydro-4,6-dimethoxy-1,3-dioxo-2H-isoindol-2-yl)phenoxy]-2,2-dimethylpentanoate;
methyl 5-[4-(1,3-dihydro-4,7-dimethoxy-1,3-dioxo-2H-isoindol-2-yl)phenoxy]-2,2-dimethylpentanoate;
methyl 5-[4-[4-(acylamino)-1,3-dihydro-1,3-dioxo-2H-isoindol-2-yl]phenoxy]-2,2-dimethylpentanoate;
4-(acylamino): methyl 5-[4-[5-(acylamino)-1,3-dihydro-1,3-dioxo-2H-isoindol-2-yl]phenoxy]-2,2-dimethylpentanoate.

The substituted phthalic anhydride used as starting materials are obtained from the following sources. The 4-chlorophthalic acid and the 4,5-dichlorophthalic acid can be purchased from Aldrich Chemical Company and converted to the corresponding phthalic anhydrides by refluxing with acetic anhydride. The 3- and 4-acylaminophthalic anhydrides are obtained by reduction and subsequent acylation of the corresponding 3- and 4-nitro compounds available from Aldrich Chemical Company. The alkyl and alkoxy substituted phthalic anhydrides are obtained by a reaction of substituted butadienes with maleic anhydride to form the corresponding tetrahydrophthalic anhydrides (A. Girardet; *Helv. Chim. Acta*, 14, 504 (1931) and C. O. Grones and R. Adams, *J. Amer. Chem. Soc.*, 45, 2439 (1923)). These substituted tetrahydrophthalic anhydrides can be dehydrogenated to the corresponding substituted phthalic anhydrides (M. S. Newman and C. O. McCleary, *JACS*, 63, 1942, (1941) and O. Brunner, H. Hofco, and R. Stein, *Monatsch.* 63, 79 (1933)).

EXAMPLE 2

Methyl 7-[4-(1,3-dihydro-1,3-dioxo-2H-isoindol-2-yl)phenoxy]-2,2-dimethylheptanoate N-[p-Hydroxyphenyl]phthalimide (5.0 g) described in Example 1 was dissolved in 100 ml of DMF and 1.13 g of $NaOCH_3$ was added. The solution was stirred at room temperature for one-half hour, then 6.25 g of methyl 2,2-dimethyl-7-iodoheptanoate was added dropwise. The mixture was stirred at room temperature overnight and then heated at reflux for two hours and concentrated on rotary evaporator. $H_2O$ (100 ml) was added and a solid was obtained. The product was extracted with EtOAc leaving the insoluble starting material behind. Concentration of the ethyl acetate solution followed by recrystallization of the resulting solid from isopropyl ether gave the purified product; mp 82°–3° C.

Calcd. for $C_{24}H_{27}NO_5$, C, 70.39; H, 6.65; N, 3.42; Found C, 70.38; H, 6.64; N, 3.39.

EXAMPLE 3

Methyl 2,2-dimethyl-5-[4-(octahydro-1,3-dioxo-2H-isoindol-2-yl)phenoxy]pentanoate A solution of 30.0 g of cis-1,2-cyclohexane dicarboxylic anhydride and 22.0 g of p-amino-phenol, and 100 ml of DMF was heated on steam bath for 18 hours and then concentrated on the rotary evaporator. The solid was suspended in 2N HCl (200 ml) and collected by filtration. Recrystallization from EtOH yielded the product; 40.1 g; mp 208° C.

A solution of 6.13 g (0.025 mol) of product from above in 100 ml of DMF plus 1.35 g of $NaOCH_3$ was stirred for 15 minutes and then 5.6 g (0.025 mol) of methyl 5-bromo-2,2-dimethylpentanoate was added dropwise at room temperature. The reaction mixture was heated with stirring on a steam bath for 18 hours and then concentrated on rotary evaporator. A solid was obtained on the addition of $H_2O$ and it was collected by filtration. Two recrystallizations from EtOAc yielded the pure product: 6.4 g; mp 109°–110° C.

Calcd. for $C_{22}H_{29}NO_5$, C, 68.19; H, 7.54; N, 3.61; Found C, 68.33; H, 7.69; N, 3.30.

I claim:

1. A compound of the formula

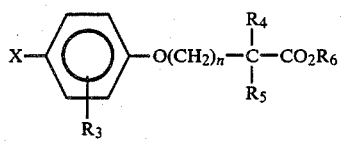

wherein X is

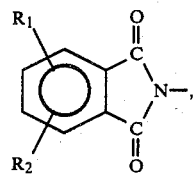 A

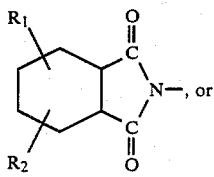 B, or

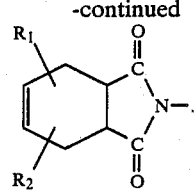 C

-continued $R_1$ and $R_2$ are the same or different and are hydrogen, halogen, a straight or branched alkyl group of from one to six carbon atoms, an alkoxy group of from one to six carbon atoms, or $CF_3$; $R_3$ is hydrogen or an alkyl group of one to four carbon atoms; n is an integer of from three to five; $R_4$ and $R_5$ are the same or different and are a straight or branched alkyl of from one to six carbon atoms or when taken together are $—(CH_2)_m—$ wherein m is an integer of from two to five; $R_6$ is hydrogen or an alkyl of from one to six carbon atoms, or a pharmaceutically acceptable base salt thereof.

2. A compound according to claim 1 wherein $R_1$ and $R_2$ are hydrogen or halogen.

3. A compound according to claim 1 wherein $R_1$ and $R_2$ are hydrogen.

4. A compound according to claim 1 wherein $R_3$ is hydrogen.

5. A compound according to claim 1 wherein n is three.

6. A compound according to claim 1 wherein n is five.

7. A compound according to claim 1 wherein $R_4$ and $R_5$ are the same or different and are a straight or branched alkyl of from one to six carbon atoms.

8. A compound according to claim 7 wherein $R_4$ and $R_5$ are methyl.

9. A compound according to claim 1 wherein $R_4$ and $R_5$ form cyclopropane.

10. A compound according to claim 1 wherein $R_6$ is methyl.

11. A compound according to claim 1 and being methyl 5-[4-(1,3-dihydro-1,3-dioxo-2H-isoindol-2-yl)phenoxy]-2,2-dimethylpentanoate.

12. A compound according to claim 1 and being methyl 7-[4-(1,3-dihydro-1,3-dioxo-2H-isoindol-2-yl)phenoxy]-2,2-dimethylheptanoate.

13. A compound according to claim 1 and being methyl 2,2-dimethyl-5-[4-octahydro-1,3-dioxo-2H-isoindol-2-yl]phenoxypentanoate.

14. An anti-arteriosclerotic pharmaceutical composition comprising an effective amount of a compound as defined in claim 1 in combination with a pharmaceutically acceptable carrier.

15. A method of treating arteriosclerosis in mammals which comprises administering to said mammals a pharmaceutical composition in accordance with claim 14 in unit dosage form.

* * * * *